United States Patent [19]

Griffiths

[11] 4,192,860
[45] Mar. 11, 1980

[54] METHODS FOR TREATING DISEASE CONDITIONS

[75] Inventor: Alan J. Griffiths, Haveringham, England

[73] Assignee: Fisons Limited, London, England

[21] Appl. No.: 900,709

[22] Filed: Apr. 27, 1978

[30] Foreign Application Priority Data

May 6, 1977 [GB] United Kingdom ............... 18995/77
May 26, 1977 [GB] United Kingdom ............... 22186/77

[51] Int. Cl.² ..................... A61K 9/14; A61K 9/00; A61K 31/35
[52] U.S. Cl. ........................................ 424/43; 424/45; 424/46; 424/283; 424/253; 424/272
[58] Field of Search .................. 424/283, 46, 43, 253, 424/272

[56] References Cited

U.S. PATENT DOCUMENTS 3,419,578 12/1968 Fitzmaurice et al. ............... 424/283

OTHER PUBLICATIONS

The Merck Veterinary Manual Third Edit. (1967), pp. 6 and 1610.
Chem. Abst. 9th Coll. Index, vol. 76–85 (1972–1976), pp. 6827cs & 6828cs.

Primary Examiner—Sam Rosen
Attorney, Agent, or Firm—Merriam, Marshall & Bicknell

[57] ABSTRACT

There is described a method for the prophylactic or curative treatment of a disease condition having an allergic basis in cats, dogs or horses or a condition of the respiratory tract having an allergic basis in cattle which comprises administering an active ingredient having sodium cromoglycate like activity to an animal suffering, or liable to suffer, from such a condition.

There are also described compositions and mixtures for use in the treatment of the animals.

12 Claims, 1 Drawing Figure

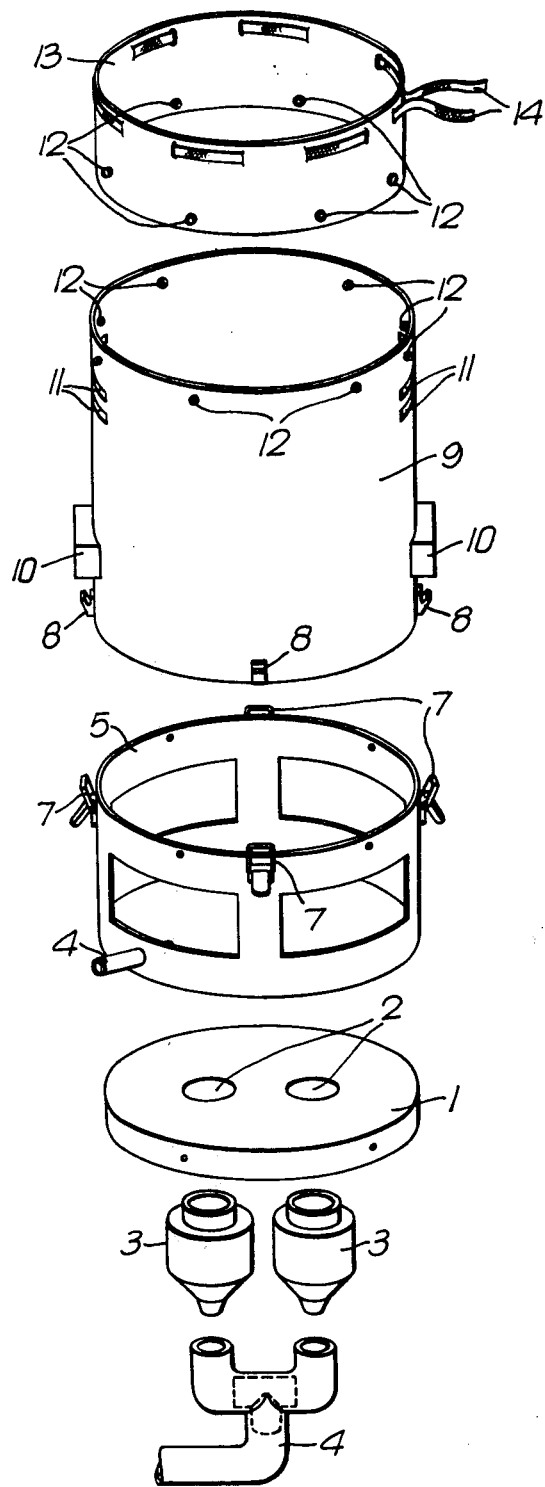

METHODS FOR TREATING DISEASE CONDITIONS

This invention relates to a novel method of treatment of animals, and to novel compositions.

According to the invention we provide a method for the prophylactic or curative treatment of a disease condition having an allergic basis in cats, dogs or horses or an allergic condition of the respiratory tract having an allergic basis in cattle, which comprises administering an active ingredient having sodium cromoglycate like activity to cattle or a horse, pig, cat or dog suffering, or liable to suffer, from such a condition.

A compound having sodium cromoglycate like activity is able to inhibit the release of pharmacological mediators which result from the in vivo combination of certain types of anti-body and specific antigen, for example the combination of reaginic antibody and specific antigen (see Example 27 of British patent specification No. 1,292,601—the rat passive cutaneous anaphylaxis test).

The active ingredients may be characterized by the following biological tests and results thereof.

The compound is first tested in the rat passive cutaneous anaphylaxis test. If the compound does not show significant inhibition of allergic manifestations at 20 mg/kg intraperitoneally (i.p.) or intravenously (i.v.) in this test, its activity is generally too low. Various other biological tests may be used to show that the compound exhibits its anti-allergy activity as an inhibitor of mediators of anaphylaxis rather than as, for example an end organ antagonist or anti-cholinergic and adenyl cyclase stimulator. Therefore, tests to see if the compound inhibits the effect of histamine, serotonin, and slow reacting substance of anaphylaxis (SRSA), that is, that the compound is an end organ antagonist of the mediators, may be employed. Such tests are well known and include contraction of guinea pig ileum in the presence of methysergide for serotonin activity. If activity is still observed in these systems, it is due to histamine action. A further check on histamine is through the spectrofluorimetric assay described by Shore, Burkhalter and Cohn, Journal of Pharmacology and Experimental Therapeutics, Vol. 127 page 182. Active ingredients according to the invention are not end organ antagonists.

If the results from these tests show that the active ingredient is not an end organ antagonist further tests may be run to show that the compound is not exhibiting its activity through anti-cholinergicity, e.g. by the reversal of acetylcholine induced guinea pig tracheal chain contraction. An active ingredient will not be anti-cholinergic.

Specific groups of active ingredients are to be found among the chromone-2-carboxylic acids, and suitable derivatives thereof, e.g., those described in British patent specifications Nos. 1,368,243; 1,144,905; 1,230,087 and West German Pat. No. 2,553,688. Other active ingredients are to be found among the xanthones, e.g., of Belgian Pat. Nos. 759,252 and 787,843 and Dutch Pat. Nos. 72,09622 and 73,06958; among the compounds of Belgian Pat. No. 792,867; among the azapurines, e.g., of Belgian Pat. No. 776,683; the oxazoles, e.g., of West German OLS No. 2,459,380; and the flavones, e.g., of Belgian Pat. No. 823,875.

Particularly preferred are the chromones and chromone like compounds of British patent specifications Nos. 1,144,905; and 1,230,087 and West German Pat. No. 2,553,688. More specifically we prefer compouns of formula I,

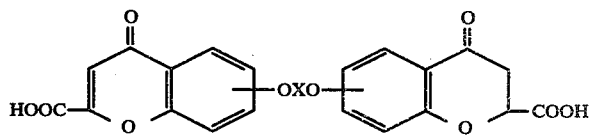

wherein X is a polymethylene chain containing 3 to 7 carbon atoms inclusive, which chain may be substituted by an —OH group, or a pharmaceutically acceptable derivative thereof.

We particularly prefer 1,3-bis(2-carboxychromon-5-yloxy)propan-2-ol or a pharmaceutically acceptable derivative, e.g., salt such as the disodium salt, thereof; this latter is commonly known as sodium cromoglycate or cromolyn sodium. As further preferred compounds there may be mentioned 6,7,8,9-tetrahydro-4-oxo-10-propyl-4H-naphtho[2,3-b]pyran-2-carboxylic acid and 6,7,8,9-tetrahydro-5-hydroxy-4-oxo-10-propyl-4H-naphthol[2,3-b]pyran-2-carboxylic acid and pharmaceutically acceptable derivatives of either thereof. Suitable pharmaceutically acceptable derivatives include salts, alkyl C 1 to 10 esters, mono-alkyl C 1 to 10 amides, di-alkyl C 1 to 10 amides or an unsubstituted amide of the 2-carboxylic acid groups.

Specific conditions to be treated by the method of the invention include those in which allergy or immune reactions play a contributory part, for example certain respiratory or pulmonary conditions. In particular there may be mentioned conditions in which antigens are involved and in which there is a shock reaction and slow reacting substance of anaphylaxis (SRS-A) is released. Specifically there may be mentioned broken wind, heaves, chronic obstructive pulmonary disease, laminitis and sweat itch in horses; and fog fever, husk, acute bovine pulmonary emphysema, bovine farmer's lung and respiratory diseases which are due, at least in part, to Respiratory Syncytial Bovine Virus (RSB) in cattle. This latter condition takes the form of an influenza like disease with dyspnoea, emphysema and foaming at the mouth. Death occurs within a few hours if no efficient treatment is given. Respiratory conditions in cattle and horses are often associated with damp climates and the feeding or presence of mouldy hay.

In cats and dogs the method of the invention may be used, particularly on oral or topical administration, to treat allergic conditions produced as a response to allergens contained in foods and food additives, in therapeutic agents, in parasitic fungi, produced by bacterial or fungal infection, or as a response to inhaled or contact antigens. Specific symptoms which may be mentioned include pruritis, characterised by excessive scratching, chewing, biting, licking or rubbing at the skin and an exaggerated scratch reflex or skin twitching; self inflicted lesions which vary in shape, size and distribution; other skin changes, characterised by generalised hyperaemia, papular reaction, oedematous plaques, oedema of head, vulva or extremities; and severe inflammatory changes leading to serous exudation and exfoliation over part of the body. Lesions are most commonly noted on the less hairy areas of the body, but their distribution varies with the agent concerned and the part of the body which comes into direct contact with the allergen. Inhaled allergens can produce 'hay fever' and 'asthma' type reactions and also conjunctivities especially in the dog. Allergic contact dermatitis is encountered most frequently in the dog.

The active ingredient may be administered by any convenient route which will produce adequate blood levels of the active ingredient or which will treat the organ causing the condition, e.g., the respiratory tract, the gut, or the skin, directly. When the condition to be treated is a condition of the respiratory tract the active ingredient may be administered directly to the respiratory tract, e.g., as a nebulised solution or as a powder aerosol which the animal is caused or forced to inhale. The powder aerosol or the nebulised solution may be administered through the mouth or nose. Thus the nebulised cloud may be produced by a conventional nebuliser, e.g., comprising an air jet blowing across the open end of a tube the other end of which is situated in the solution to be nebulised, and an impinger on which the larger drops of nebulised solution are collected. The nebuliser may be powdered by a compressed air, nitrogen or oxygen supply or by a hand operated, mechanical or preferably by an electrical pump.

The nebuliser or nebulisers are preferably mounted in a device comprising an inhalation chamber which is adapted to fit over the animals nose and mouth. The device is preferably cylindrical or bag shaped and is preferably made from material, and preferably fairly rigid material, which will be sufficiently robust to be used in veterinary practice, e.g., fiberglass or polypropylene. The device is also preferably provided with one or more ports or valves permitting the animal to exhale with reasonable ease. The device is also preferably provided with means for fixing it over the animal's nose and mouth, e.g., straps to tie behind the head and ears. In order to minimise the loss of nebulised solution from the device, other than by inhalation, the device may comprise means for sealing the inhalation chamber over the animal's face, for example a rubber or flexible seal which fits and can optionally be tightened around the animal's head, e.g., by means of draw straps. The powder aerosol may be produced by a pressure pack formulation of the active ingredient or by means of the device of British Pat. No. 1,182,779, which is commercially available under the Trade Mark 'Spinhaler.' The nebulised solution or the powder aerosol may be transferred from the generating device to the animal's nose or mouth as described above or by means of a flexible tube provided in the case of nasal administration with adaptors for insertion in one or more nostrils, and, in the case of oral inhalation administration with means that will not be crushed in the mouth for transferring the nebulised solution or the powder aerosol to the animal's airways. The active ingredient may also be administered intravenously, intramuscularly or preferably subcutaneously.

The active ingredient to be administered by the method of the invention may if desired be admixed with one or more other compounds which are tolerated by the animal by the chosen method of administration, for example for inhalation administration with water, coarse lactose or, for pressurised aerosol formulations, with suitable propellants and surfactants. The active ingredient may also be admixed with a compound which prevents the release of SRS-A (Slow Releasing Substance of Anaphylaxis) or antagonises SRS-A when released. Suitable anti SRS-A compounds include diethylcarbamazine. Such mixtures may be used in accordance with the method of the invention. Alternatively the active ingredient may be administered within a short time of, or simultaneously with, the administration of the anti SRS-A compound. When diethylcarbamazine is used a dosage of from about 15 to 25 mg/kg, e.g. 20 mg/kg, of animal body weight may be used. For oral administration the active ingredient may be admixed with inert diluents, such as talc, dextran, lactose, calcium phosphate, water etc. The active ingredient may also be admixed with the animal's foodstuff, e.g., milk, or with other matter which it is desired to administer to the animal orally. Thus the active ingredient may be admixed with desirable trace elements such as copper, cobalt, manganese or a mixture thereof; with one or more vitamins, e.g., vitamins A, D, $B_1$, $B_2$, $B_6$, $B_{12}$, E (or other anti-oxidants) or a mixture thereof; antibiotics (to assist in the prevention of a neonatal scour), for example broad spectrum antibiotics such as chlortetracycline hydrochloride, oxytetracyclin and nitrofurans; absorption aids, e.g., certain amino acids and/or electrolytes; immunoglobulins; or corticosteroids.

Particular compositions for oral administration which may be mentioned are fluid compositions, e.g., a drench, which may be administered with a drenching gun or bottle or a similar device adapted to administer a metered dose to the animal. The drench may be supplied in the form of a wettable powder which can then be dispersed or dissolved in water by the user. Such a powder may compromise the active ingredient, a colloid to make the drench of suitable viscosity for the gun, and a surface active agent to assist dispersion or dissolution of the powder in water. The drench may also be supplied in liquid form in which case it is desirable to incorporate a preservative, e.g., chloroform, glycerin or sodium benzoate. The active ingredient may also be presented in the following forms:

as a tablet containing active ingredient, binder, moistening agent, disintegrant and lubricant; or as a capsule containing active ingredient, binder, moistening agent and lubricant; or as a pill or bolus containing active ingredient and syrup or treacle; or as a paste containing active ingredient, gum and preservative; or as an aerosol pack containing active ingredient, surface active agent, propellant and optionally water.

The aerosol, drench and paste compositions may also, if desired, contain a suitable flavouring to help prevent rejection of the composition by the animal. The compositions should of course be in such a form that the required dose may be administered easily, e.g., as a single unit dose, to the animal. Preferred compositions from the point of view of ease and certainty of oral administration are those which are solids or pastes.

The active ingredient may be administered orally to the animal in conventional manner, for example tablets, capsules, pills and boluses may be placed at, or shot or flicked into the back of the animals mouth and pastes may be smeared carefully on tongue, teeth and the inside of the animals mouth. The active ingredient may also be administered by other techniques, for example liquids and pastes may be administered from a bottle or gun adapted to eject a metered dose, and aerosol compositions may also be put up in containers adapted to eject a metered dose. Such bottles, guns and containers containing a composition comprising the active ingredient from a further feature of our invention.

The dosage of active ingredient to be administered will of course vary with the active ingredient, the condition to be treated, with its location and severity, with the method of administration and the size of the animal. However we have found that in general the active ingredient may be administered intravenously, intramuscularly or subcutaneously at a daily dosage of up to about 15 mg/kg, e.g., from about 5 to 15 mg/kg, and preferably about 10 mg/kg of animal body weight. When i.v. administration is used the administration preferably takes at least 60 seconds. Suitable daily dosages for inhalation administration, e.g., as a nebulised solution, are generally up to 160 mg and are preferably in the range 40 to 160 mg, and more preferably 40 to 80 mg per animal per day.

For gastrointestinal disturbances we prefer to administer the active ingredient orally. Thus for cats and dogs we prefer to administer a daily dosage of up to 250 mg, and preferably from 25 to 250 mg of active ingredient.

The dosages mentioned above may be administered as split doses from 1 to 4 times, and preferably once or twice, a day.

The method of the invention when applied to cattle, pigs or horses enhances the weight gain of the animal as compared to untreated animals.

The invention is illustrated, but in no way limited by the following Examples.

EXAMPLE 1

Chronic Obstructive Pulmonary Disease in the Horse

Two horses sensitised to *M. faeni* were used. The *M. faeni* challenge is given by nebulising a suspension of spores in a Wright nebuliser; directing this spore laden atmosphere via a length of rubber tubing into a bucket secured to the muzzle of the horse; and finally by the normal inhalation of the animal to the respiratory tract.

Nebulised disodium cromoglycate is administered to the horse by inhalation from a mask attached and sealed to the muzzle. This consists of a plastic bucket into the walls of which are welded 4 nebuliser units. These are positioned opposite the external nares of the horse and 3–4 inches from the base of the bucket. Into the base of the bucket is secured a one way valve to allow exhalation. The nebuliser units are situated such that in use they are in the horizontal position. Each unit is charged with 2 mls of disodium cromoglycate 1% aqueous solution and operated from a Wright pump from which the flow rate is reduced to 9 liters/minute by means of a bleed valve.

For the initial trial the horse was treated for four days receiving 80 mg of disodium cromoglycate as a single dose on each of the days. It was then challenged at intervals after the treatment period with *M. faeni* using clinical appearance, auscultation of the chest and changes in intra-thoracic pressure and in arterial oxygen pressure as the main indicators of response to challenge.

The horse did not react to challenge up to seven days post treatment period, but was not protected at 4 weeks after the treatment period.

In the second trial the 4 day treatment period with the same levels of disodium cromoglycate afforded protection to the *M. faeni* challenge at 10 days, but not at 17 days post treatment.

The final trials involved the determination of the protective period of a single treatment of disodium cromoglycate.

In the first of these trails a single dose of 80 mg of disodium cromoglycate was protective at 2 days, but not at 4 days post treatment. In the second, a single dose of 160 mg of disodium cromoglycate was protective at 2 days, but not at 4 days post treatment. In the second, a single dose of 160 mg of disodium cromoglycate was not protective 4 days post treatment.

In a second horse the 4 day treatment schedule as above was protective at 10 days post treatment.

EXAMPLE 2

Six dogs and one cat were used. Disodium cromoglycate in gelatin capsules containing 25 mg or 100 mg active material were administered orally once a day for the trial period.

Daily clinical observations were made for all animals and changes in skin condition recorded.

Results

The response of the individual cases to treatment are detailed below:

1. Cat—Food allergy—Beef: Generalised pruritis. Skin macroscopically normal but irritation leading to self-inflicted skin damage following challenge with cooked beef.

Treatment

1×25 mg disodium cromoglycate per day, starting 24 hours after the animal was placed on a beef diet. All irritation resulting from the beef was resolved within the following 24 hours. The treatment was continued for seven days during which time the animal remained in good health with no evidence of irritation despite being kept on the beef diet. Cessation of treatment resulted in a recurrence of irritation.

3. Dog—Retriever Allergy: Severe pollen contact allergy not controlled by steroids after initial success on that therapy.

Treatment

1×100 mg disodium cromoglycate per day initially, increased to 1×200 mg per day. No improvement noted on the lower dose. Seven days later the dose was increased to 200 mg disodium cromoglycate per day, when some improvement was obtained. However, the skin thickening and hyperaemia remained and the animal indulged in bouts of scratching.

4. Dog—Alsation, Food Allergy—Pork: Allergy present for at least twelve months with marked secondary changes and extensive cutaneous staphylococcal infection.

Treatment

1×100 mg disodium cromoglycate per day. A slight improvement was noted over the seven day trial.

5. Dog—Terrier, Food Allergy—cows milk: The allergy had previously been well controlled on betamethasone treatment.

Treatment

1×100 mg disodium cromoglycate per day. Steroid therapy was replaced by disodium cromoglycate for a four day period. The skin irritation returned but was not severe.

6. Dog—Setter, Food Allergy—cows milk: The allergy caused generalised skin irritation plus a pollen contact allergy producing regional changes. The animal did not tolerate steroid therapy which resulted in excessive thirst, urination and pseudo pregnancy.

Treatment

1×100 mg disodium cromoglycate per day. The irritation appeared to lessen over the back during the seven day trial.

7. Dog—Terrier, Food Allergy—mutton: The condition was well controlled with steroids.

Treatment

1×100 mg disodium cromoglycate per day. Fairly good control was obtained during the five day trail after the first 48 hours.

8. Dog—Retriever/Labrador, Food Allergy—beef: The allergic skin condition had an associated bacterial infection.

Treatment

1×100 mg disodium cromoglycate per day. The clinical allergic condition and bacterial infection responded very well to the treatment.

A device suitable for administration of a nebulised solution to an animal is illustrated in the attached FIGURE which represents an exploded view of the device.

In the FIGURE a base plate 1 is provided with two nebuliser nozzle retaining holes 2 into which two nebulisers 3 are adapted to fit. The nebulisers are connected to a compressed air delivery system 4. The base plate 1 is mounted in a frame 5 in which the compressed air delivery system 4 is supported. The frame 5 is provided with toggle clamps 7 which are adapted to fit over the toggle clamp hooks 8 on the inhalation chamber 9. The inhalation chamber 9 is provided with two exhalation valves 10, with head strap slots 11 and with press studs 12. The inhalation chamber 9 is adapted to fit onto the flexible (rubber) seal 13 by means of the press studs 12 and the flexible seal 13 is provided with a draw tape 14.

In operation the inhalation chamber 9 and the flexible seal 13 are placed over the animals head and the frame 5 in which the nebulisers 3 (which have been filled with an aqueous solution of active ingredient), the base plate 1 and the compressed air delivery system 4 are mounted is clipped onto the inhalation chamber by means of the clips 7 and the hooks 8. The nebulisers are then actuated and a supply of nebulised solution provided for the animal to inhale for the appropriate time to provide the required dose of active ingredient.

I claim:

1. A method for curative treatment of a disease condition in cats, dogs horses or cattle as follows:

(a) in horses: broken wind, heaves, chronic pulmonary disease, laminitis or sweat itch;

(b) in cattle: fog fever, husk, acute bovine pulmonary emphysema, bovine farmer's lung and respiratory diseases due to Respiratory Syncytial Bovine Virus;

(c) in cats or dogs: allergic condition produced in response to allergens present in foods or food additives, in therapeutic agents, in parasitic fungi, produced by bacterial or fungal infection, or as a response to inhaled or contact antigens;

which method comprises administering an effective amount of an active ingredient having sodium cromoglycate like activity to cattle or to a horse, pig, cat or dog suffering from such a condition.

2. A method according to claim 1 wherein the active ingredient is a compound of formula I,

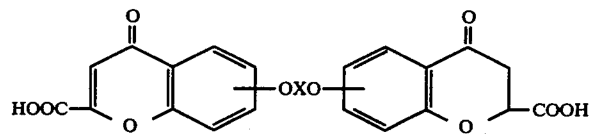

I wherein X is a polymethylene chain containing 3 to 7 carbon atoms inclusive, which chain may be substituted by an —OH group, or a pharmaceutically acceptable salt thereof.

3. A method according to claim 1, wherein the active ingredient is sodium cromoglycate.

4. A method according to claim 1, wherein the condition is a pulmonary condition in the horse or in cattle in which allergy or immune reactions play a contributory part.

5. A method according to claim 1, wherein broken wind, heaves, chronic pulmonary disease, laminitis or sweat itch, is treated in a horse.

6. A method according to claim 1, wherein fog fever, husk, acute bovine pulmonary emphysema, bovine farmer's lung or a respiratory disease due to Respiratory Syncytial Bovine Virus is treated in cattle.

7. A method according to claim 1, wherein an allergic condition produced as a response to allergens contained in foods and food additives, in therapeutic agents, in parasitic fungi, produced by bacterial or fungal infection, or as a response to inhaled or contact antigens is treated in a cat or dog.

8. A method according to claim 1, wherein the active ingredient is administered directly to the respiratory tract, the gut or the skin.

9. A method according to claim 1, wherein the condition is of the respiratory tract and the active ingredient is administered as a nebulised solution or as a powder aerosol.

10. A method according to claim 1, wherein the active ingredient is administered intravenously, intramuscularly or subcutaneously at a dosage of from 5 to 15 mg per kg of animal body weight.

11. A method according to claim 1, wherein a dosage of 40 to 160 mg is administered by inhalation.

12. A method according to claim 1, wherein a daily dosage of from 25 to 250 mg of active ingredient is administered to a cat or dog.

* * * * *

UNITED STATES PATENT AND TRADEMARK OFFICE
CERTIFICATE OF CORRECTION

PATENT NO. : 4,192,860

DATED : March 11, 1980

INVENTOR(S) : ALAN J. GRIFFITHS

It is certified that error appears in the above-identified patent and that said Letters Patent are hereby corrected as shown below:

Col. 1, line 68, "759,252" should be --759,292--.

Col. 2, line 9, "compouns" should be --compounds--.

Col. 2, line 31, "naphthol" should be --naphtho--.

Col. 3, line 8, "conjunctivities" should be --conjunctivitis--.

Col. 3, line 27, "powdered" should be --powered--.

Col. 5, line 5, "from", should be --form--.

Col. 6, line 6, "trails" should be --trials--.

UNITED STATES PATENT AND TRADEMARK OFFICE
CERTIFICATE OF CORRECTION

PATENT NO. : 4,192,860
DATED : March 11, 1980
INVENTOR(S) : ALAN J. GRIFFITHS

It is certified that error appears in the above-identified patent and that said Letters Patent are hereby corrected as shown below:

Formula, <u>Cols. 2 and 8</u>, the right-most vertical bond should be a double bond:

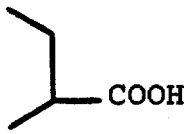   should be   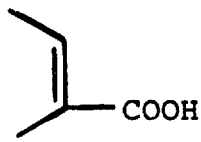

Signed and Sealed this

*Twenty-first* Day of *April 1981*

[SEAL]

*Attest:*

RENE D. TEGTMEYER

*Attesting Officer*   *Acting Commissioner of Patents and Trademarks*